United States Patent [19]

Weiss et al.

[11] Patent Number: 4,956,503

[45] Date of Patent: Sep. 11, 1990

[54] PROCESS FOR THE PREPARATION OF N-CYANOETHANIMIDIC ACID ESTERS

[75] Inventors: Stefan Weiss; Helmut Krommer; Karl-Heinz Neuhauser, all of Trostberg, Fed. Rep. of Germany

[73] Assignee: SKW Trostberg Aktiengesellschaft, Trostberg, Fed. Rep. of Germany

[21] Appl. No.: 339,806

[22] Filed: Apr. 18, 1989

[30] Foreign Application Priority Data

May 4, 1988 [DE] Fed. Rep. of Germany ....... 3815084

[51] Int. Cl.$^5$ .......................................... C07C 261/04
[52] U.S. Cl. ..................................... 564/106; 564/103
[58] Field of Search .............................. 564/106; 558/9

[56] References Cited

U.S. PATENT DOCUMENTS 3,225,077 12/1965 Schaefer et al. ...................... 558/9

FOREIGN PATENT DOCUMENTS 3411203 6/1985 Fed. Rep. of Germany ...... 564/106

Primary Examiner—Glennon H. Hollrah
Assistant Examiner—Susan P. Treanor
Attorney, Agent, or Firm—Perman & Green

[57] ABSTRACT

A process for the preparation of N-cyanoethanimidic acid esters by reacting orthoacetic acid esters with cyanamide. The reaction is carried out in alcoholic solution in the presence of an acid catalyst. N-cyanoethanimidic acid esters can be prepared in this manner in a high yield and high state of purity, with a low technical outlay and in an environmentally safe manner, free of dangerous by-products.

13 Claims, No Drawings

PROCESS FOR THE PREPARATION OF N-CYANOETHANIMIDIC ACID ESTERS

BACKGROUND OF THE INVENTION

1. Field of the Invention

The present invention relates to the preparation of N-cyanoethanimidic acid esters, particularly the methyl and ethyl esters thereof having the formula I:

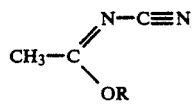

in which R is $CH_3$ or $C_2H_5$.

Such esters are of industrial importance as starting materials for the preparation of heterocyclic compounds, such as, for example, 2-amino-4-methoxy-6-methyl-s-triazine, from which important plant protection agents are prepared.

2. Description of the Prior Art

It is known to prepare N-cyanoethanimidic acid esters in a two-stage process from acetonitrile, gaseous hydrogen chloride, alcohol and cyanamide, as disclosed in German Patent Specification No. 3,411,203. In this process the corresponding ethanimidic acid ester-hydrochlorides are formed in a first reaction between acetonitrile, anhydrous hydrogen chloride and methanol or ethanol, and these ester-hydrochlorides are converted into the corresponding N-cyanoethanimidic acid esters in a second reaction with cyanamide, with the elimination of ammonium chloride.

It is a disadvantage of this process that requires the use of anhydrous, and extremely corrosive, hydrogen chloride gas. This not only necessitates the use of very expensive, corrosion-resistant special equipment, but also the use of special safety measures to protect the environment, which makes the process very expensive. Another disadvantage results from the fact that large amounts of ammonium chloride are produced in this process, which requires expensive disposal procedures.

A possible alternative, described in the literature, is the preparation of ethyl N-cyanoethanimidates by reacting triethyl orthoacetate with cyanamide in the presence of two molar equivalents of acetic anhydride (cf. in this connection K. R. Huffmann and F. C. Schaefer, J. Org. Chem. 28 (1963) page 1816). In re-working this process, however, it has been found that it is purely a laboratory method which cannot be applied on an industrial scale because of serious disadvantages. This is because by-products are formed in this reaction, comprising two moles of ethylacetate and two moles of acetic acid per mole of triethyl orthoacetate. The separation of these by-products from the reaction product, during or after the reaction, causes considerable problems. On an industrial scale, a temperature of 160° to 190° C. is required for the continuous removal by distillation of the acetic acid formed, and at this temperature ethyl N-cyanoethanimidate decomposes partially or undergoes rearrangement into N-cyano-N-ethylacetamide by a Chapman rearrangement. In addition, reaction mixtures containing cyanamide should not be heated above 120° C. for reasons of safety. A further disadvantage is the relatively low purity of product, complete separation from the acetic acid and unreacted acetic anhydride causing enormous difficulties in spite of an elaborate vacuum distillation at 25 to 30 mbar. Finally, this suggested process cannot be used for the preparation of methyl N-cyanoethanimidate.

SUMMARY OF THE INVENTION

The present invention is concerned with developing a process for the preparation of N-cyanoethanimidic acid esters, by reacting orthoacetic acid esters with cyanamide, which process does not have the disadvantages of the prior known processes, but makes it possible to prepare, with a low technical outlay and in an environmentally harmless manner, N-cyanoethanimidic acid esters in a good yield and a high state of purity.

This objective is achieved in accordance with the present invention by carrying out the present reaction in an alcoholic solution, in the presence of an acid catalyst, to produce N-cyanoethanimidic acid esters. The reaction is unexpectedly problem-free, requires only a low outlay for equipment and minimum safety measures, and has no disadvantages in respect of yield and purity.

DETAILED DESCRIPTION

The process according to the present invention comprises reacting an orthoacetic acid ester, in particular the methyl or ethyl ester, with cyanamide in the presence of an acid catalyst and in an alcoholic solution.

Within the scope of the present invention, acid catalysts are to be understood to include compounds which contain or liberate $10^{-6}$ to $10^{-1}$ mole of protons per mole of orthoacetic acid ester in the reaction mixture. Such catalysts comprise for example, inorganic acids, in particular mineral acids, such as, for example, sulfuric or phosphoric acid, and also organic acids, such as, for example, formic or acetic acid. For reasons of expense, sulfuric acid is regarded as preferred.

The amount of the catalyst depends essentially on the amount of orthoacetic acid ester employed, less than 1% by weight of catalyst generally being required, relative to the weight of orthoacetic acid ester, particularly if strong acids are used. If concentrated sulfuric acid is used, the preferred quantity range is, for example, 0.1 to 0.5% by weight of concentrated sulfuric acid.

In adding the catalyst it must be borne in mind that technical orthoacetic acid esters already have a weakly acid reaction and that commercially available cyanamide can already contain stabilizers with an acid reaction. In certain circumstances this can have the result that, if these acidic technical starting materials are used, the required amount of catalyst is already present and therefore an extra addition is no longer necessary. In this particular embodiment, however, somewhat longer reaction times must be expected.

It is essential to the invention that the reaction is carried out in alcoholic solution, in particular in methanol and ethanol, since in this case a particularly rapid and selective reaction results. In this regard it is not absolutely necessary to introduce the alcohol into the reaction solution either on its own or mixed with one of the reactants, since two moles of alcohol per mole of orthoacetic acid ester are liberated during the reaction and this then acts as the reaction medium.

In order to achieve particularly high yields it is necessary to employ at least one mole of orthoacetic acid ester per mole of cyanamide, and, as a rule, an excess of 0.05 to 0.1 mole of orthoacetic acid ester per mole of cyanamide is adequate. Although a larger excess is possible in principle, it does not afford any benefit and therefore is not economical.

Although the reaction occurs at temperatures above 30° C., preferably it is carried out at temperatures from 40° to 140° C., most preferably at 60° to 90° C., for the sake of better time yields, the reaction times being usually 3 to 9 hours.

Normally the reaction is carried out at the boiling point of the particular reaction medium under normal pressure. The reaction can, of course, also be carried out under higher or lower pressure, if this is desirable for technical reasons.

Carrying out the process according to the invention is technically very simple and without problems using customary equipment. Normally, a mixture of cyanamide and orthoacetic acid ester is prepared and is then heated, with the addition of the acid catalyst, under reflux (60° to 90° C.) until the reaction is complete (3 to 8 hours).

When large batches are used on an industrial scale, it has proved particularly advantageous to take the orthoacetic acid ester and the catalyst, initially heat the mixture to 80° to 90° C. and then gradually introduce the cyanamide, in the form of an alcoholic solution, in the course of 1 to 2 hours while the mixture is stirred and refluxed. When the addition of the cyanamide solution is complete, the mixture is heated under reflux for a further 2 to 8 hours.

The only by-product formed during the reaction of the methyl or ethyl orthoacetate is methanol or ethanol, respectively. This has the advantage that the reaction mixture can be worked up very simply.

The crude product obtained after the corresponding alcohol has been stripped off or distilled off is so pure that, as a rule, it can be further processed directly without distillation. In many cases it is not even necessary to remove the alcohol, because the alcoholic reaction mixture is suitable for certain further uses in this form.

If, on the other hand, a very pure N-cyanoethanimidic acid ester is required, the crude product may be purified by distillation, preferably in vacuo. The yields of pure product are usually 91 to 97%.

The process according to the present invention is distinguished, above all, by its very low technical outlay, its lack of harm to the environment and its very good yields, so that the requirements for an industrial scale process are excellently fulfilled.

The following examples are intended to illustrate the invention in greater detail, without, however, limiting it thereto.

EXAMPLE 1

1021 g (8.4 mol) of technical trimethyl orthoacetate (98.8% pure) (pH 4.9=$1.6 \times 10^{-6}$ mol of free protons per mole of trimethyl orthoacetate) were initially taken and heated to 80° C. A solution of 338 g (8 mol) of technical cyanamide (99.5% pure) having a pH of 5.0 as a 50% strength aqueous solution (=$8.4 \times 10^{-7}$ mol of free protons per mole of cyanamide) in 240 g of methanol was then added dropwise in the course of 1 hour with vigorous stirring at an external temperature (bath temperature) of 80° C. The total amount of free protons employed was $2.4 \times 10^{-6}$ mol of protons per mole of trimethyl orthoacetate. When the addition of the methanolic cyanamide solution was complete, the reaction mixture was heated under reflux for a further 8 hours. The reaction mixture was then concentrated in a rotary evaporator under a water pump vacuum at a water bath temperature of 60° C. 757 g (96.5%) of crude product were obtained and were subsequently distilled in vacuo.

The yield was 738.3 g (94.1%) of methyl N-cyanoethanimidate having a boiling point of 80.5 to 82° C./16 mbar (literature 98° to 99° C./33 mbar) and a purity, determined by gas chromatography, of 99.8%. The determination by gas chromatography was carried out under the following conditions:

| | |
|---|---|
| Equipment: | Carlo Erba Fractovap 2300 |
| Column: | Chromosorb WAW DMCS 5 m ¼" |
| Column temperature: | 150° C. |
| Injector temperature: | 150° C. |
| Detector temperature: | 150° C. |
| Detector: | WLD |
| Carrier gas: | He/2 bar |
| Amount of sample (charge): | 4 µl |
| Evaluation: | over total area |
| Retention time: | 373 seconds |

$C_4H_6N_2O$ (98.10 g/mol): Calculated C 48.97%, found C 48.81%. Calculated H 6.16%, found H 6.13%. Calculated N 28.55%, found N 28.37%.

EXAMPLE 2

1021 g (8.4 mol) of technical trimethyl orthoacetate (98.8% pure) and 2 g of concentrated sulfuric acid (96% strength=$4.7 \times 10^{-3}$ mole of free protons per mole of trimethyl orthoacetate) were initially taken and heated to 80° C. A solution of 338 g (8 mol) of technical cyanamide (99.5% pure) in 240 g of methanol was then added dropwise in the course of 1 hour with vigorous stirring at an external temperature (bath temperature) of 80° C. When the addition of the methanolic cyanamide solution was complete, the reaction mixture was heated under reflux for a further 6 hours. The reaction mixture was then concentrated in a rotary evaporator under a water pump vacuum at a water bath temperature of 60° C. 756 g (96.3%) of crude product were obtained and were subsequently distilled in vacuo.

The yield was 739 g (94.2%) of methyl N-cyanoethanimidate having a boiling point of 80.5° to 82° C./15 mbar (literature 98° to 99° C./33 mbar) and a purity of 100%, determined by gas chromatography (injection and column temperatures: 150° C.)

$C_4H_6N_2O$ (98.10 g/mol).

EXAMPLE 3

973 g (8 mol) of technical trimethyl orthoacetate (98.8% pure) and 2 g of concentrated sulfuric acid (96% strength=$4.9 \times 10^{-3}$ mol of free protons per mole of trimethyl orthoacetate) were initially taken and were heated to 80° C. A solution of 338 g (8 mol) of technical cyanamide (99.5% pure) in 240 g of methanol was then added dropwise in the course of 1 hour with vigorous stirring at an external temperature (bath temperature) of 80° C. When the addition of the methanolic cyanamide solution was complete, the reaction mixture was heated under reflux for a further 6 hours. The reaction mixture was then concentrated in a rotary evaporator under a water pump vacuum at a water bath temperature of 60° C. 743 g (94.7%) of crude product were obtained and were subsequently distilled in vacuo.

The yield was 719 g (91.6%) of methyl N-cyanoethanimidate having a boiling point of 80.5 to 82° C./16 mbar (literature 98° to 99° C./33 mbar) and a purity of 99.9%, determined by gas chromatography (injection and column temperatures: 150° C.)

$C_4H_6N_2O$ (98.10 g/mol): Calculated C 48.97%, found C 48.62%. Calculated H 6.16%, found H 6.11%. Calculated N 28.55%, found N 28.54%.

EXAMPLE 4

169 g (4 mol) of 99.5% pure technical solid cyanamide were dissolved in 511 g (4.2 mol) of technical trimethyl orthoacetate having a purity of 98.8%. After 2 g of concentrated sulfuric acid (96% strength = $9.3 \times 10^{-3}$ mol of free protons per mol of trimethyl orthoacetate) had been added, the mixture was heated under reflux for 6 hours with stirring. The methanol formed in the reaction was distilled off on a rotary evaporator at 60° C. under a water pump vacuum. This left 390 g (99.4%) of crude methyl N-cyanoethanimidate as residue, and this was subsequently distilled in vacuo.

The yield of pure material was 378.2 g (96.4% overall yield) of methyl N-cyanoethanimidate of boiling point 80.5° to 82° C./16 mbar. The product had a purity of 100% according to analysis by gas chromatography.

$C_4H_6N_2O$ (98.10 g/mol): Calculated C 48.97%, found C 48.62%. Calculated H 6.16%, found H 6.10%. Calculated N 28.55%, found N 28.40%.

EXAMPLE 5

A solution of 21.2 g (0.5 mol) of technical cyanamide (99% pure) having a pH, as a 50% strength aqueous solution, of 4.8 (= $1.3 \times 10^{-6}$ mol of free protons per mol of cyanamide) in 82.8 g (0.5 mol) of technical triethyl orthoacetate (pH 4.2 = $1.2 \times 10^{-5}$ mol of protons per mol of triethyl orthoacetate) was heated under reflux for 10 hours. The total amount of free protons employed was $1.33 \times 10^{-5}$ mol of protons per mol of triethyl orthoacetate. The reaction solution was then concentrated on a rotary evaporator at a water bath temperature of 60° C. The residue was then distilled in vacuo, when 53.7 g (95.8%) of ethyl N-cyanoethanimidate having a purity of 99.9% (according to analysis by gas chromatography) passed over at 87° to 88° C. under a pressure of 12 mbar.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

We claim:

1. A process for the preparation of N-cyanoethanimidic acid esters consisting essentially of reacting orthoacetic acid esters with cyanamide in the presence of an acid catalyst and in an alcoholic reaction medium at a temperature up to about 90° C., said acid catalyst comprising one or more compounds which contain, or liberate in the reaction mixture, $10^{-6}$ to $10^{-1}$ mole of protons per mole of orthoacetic acid ester.

2. The process of claim 1 wherein the acid catalyst comprises an inorganic mineral acid.

3. The process of claim 2 wherein the mineral acid comprises sulfuric acid.

4. The process of claim 1 wherein the acid catalyst comprises an organic acid.

5. The process of claim 4 wherein the organic acid comprises acetic acid.

6. The process of claim 1 wherein the amount of the catalyst is less than 1% by weight relative to the orthoacetic acid ester employed.

7. The process of claim 6 wherein the amount of catalyst is between 0.1 and 0.5% by weight relative to the orthoacetic acid ester employed.

8. The process of claim 1 wherein the orthoacetic acid ester comprises a technical grade of orthoacetic acid ester which is acidic to provide said acid catalyst.

9. The process of claim 1 wherein the cyanamide comprises a technical grade cyanamide containing acidic stabilizer(s) to provide said acid catalyst.

10. The process of claim 1 wherein said alcoholic solution comprises ethanol.

11. The process of claim 1 wherein at least one mole of orthoacetic acid ester is present per mole of cyanamide.

12. The process of claim 11 wherein an excess of 0.05 to 0.1 mole of orthoacetic acid ester is present per mole of cyanamide.

13. The process of claim 1 wherein the reaction temperature is between 60° and 90° C.

* * * * *